United States Patent [19]
Holdren

[11] Patent Number: 6,062,754
[45] Date of Patent: May 16, 2000

[54] UNIVERSAL COORDINATIONAL SUPPORT FOR ASSISTING PHYSICALLY IMPAIRED INDIVIDUALS

[76] Inventor: Howard P. Holdren, R.R. 1, Box 353, Ulster, Pa. 18850

[21] Appl. No.: 09/193,622

[22] Filed: Nov. 17, 1998

Related U.S. Application Data

[63] Continuation-in-part of application No. 08/845,219, Apr. 21, 1997, abandoned.

[51] Int. Cl.[7] .................................................. B43K 29/00
[52] U.S. Cl. ............................... 401/48; 401/6; 434/166; 601/33; 623/65
[58] Field of Search .................................. 601/33; 623/65; 401/6, 48; 434/162, 163, 166; 602/20, 62; 33/18.1, 26, 1 M, 1 PT, 430, 435

[56] References Cited

U.S. PATENT DOCUMENTS 4,149,532  4/1979  Terry et al. .............................. 623/65
4,585,363  4/1986  McGuire .

*Primary Examiner*—Bruce Snow
*Attorney, Agent, or Firm*—Salzman & Levy

[57] ABSTRACT

A device that assists the motor control of a physically impaired individual, allowing the person to do useful work by providing a coordinational support in all three orthogonal dimensions. The support has a linkage that can be manipulated in both the horizontal plane and the vertical plane. The device is easily assembled and disassembled by means of threaded elements that fabricate the linkage.

18 Claims, 11 Drawing Sheets

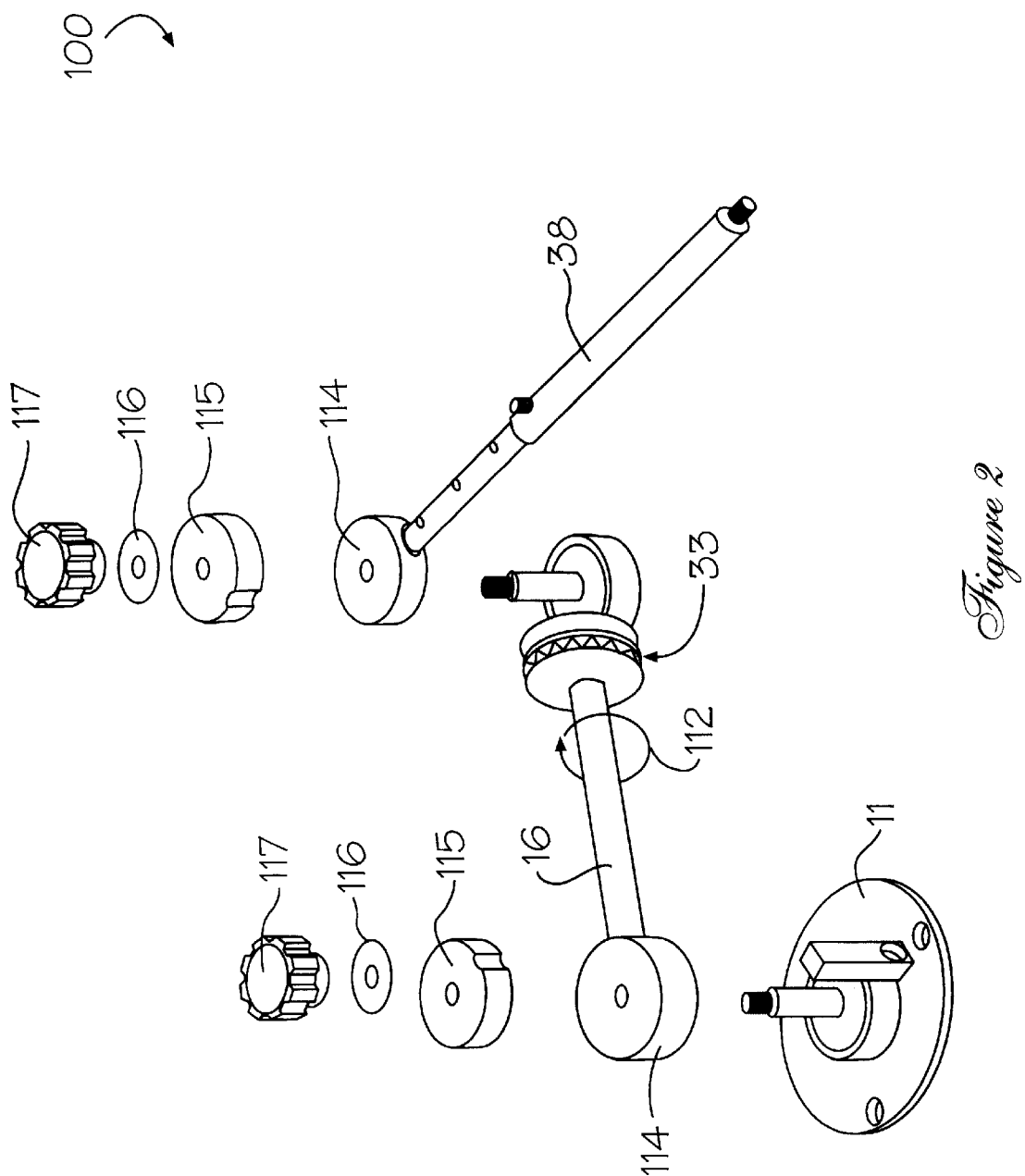

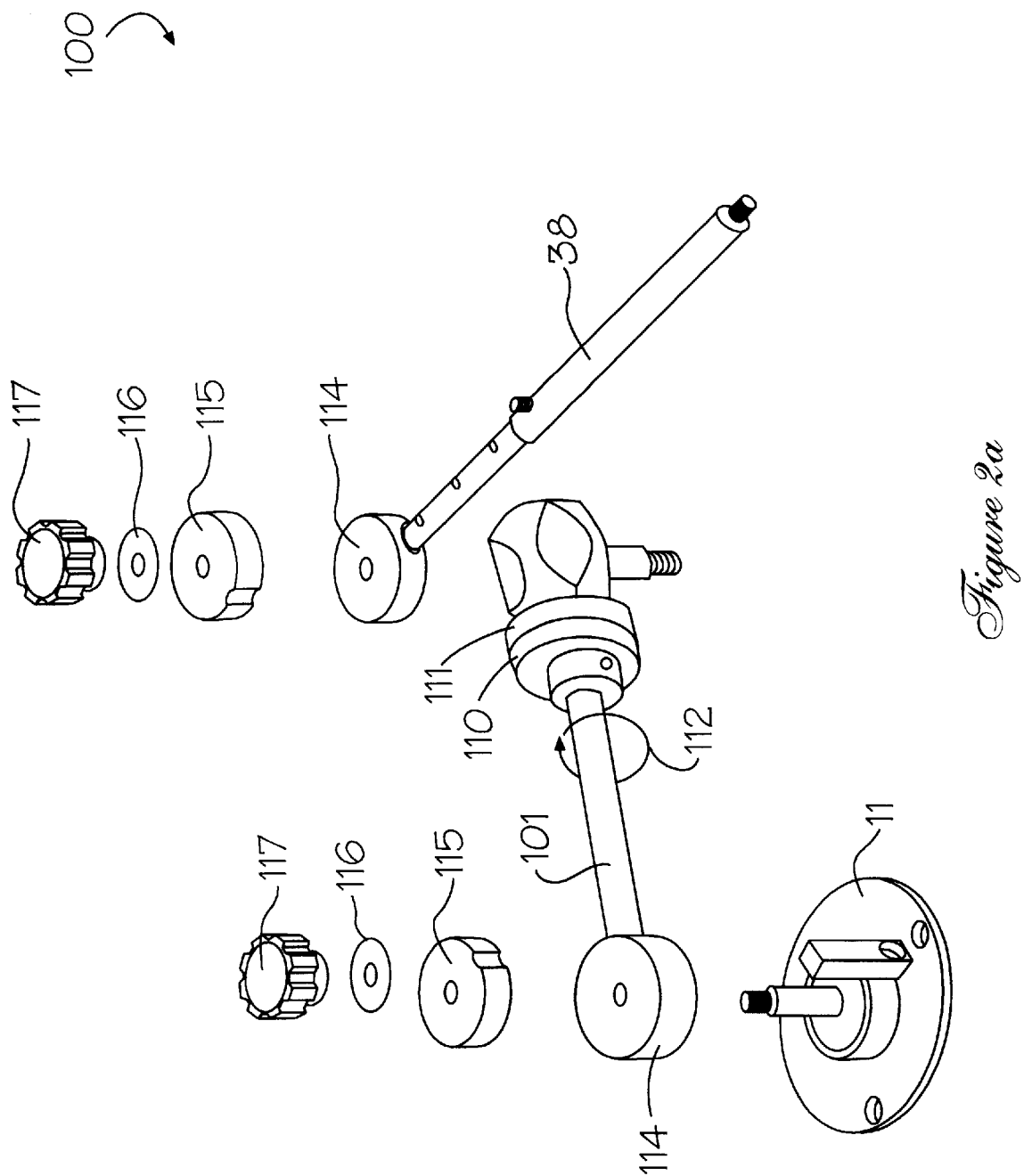

UNIVERSAL COORDINATIONAL SUPPORT FOR ASSISTING PHYSICALLY IMPAIRED INDIVIDUALS

RELATED PATENT APPLICATION

This application is a continuation-in-part of the parent application, Ser. No. 08/845,219, filed Apr. 21, 1997, now abandoned. The teachings expressed in the parent application are meant to be incorporated herein by way of reference.

FIELD OF THE INVENTION

The present invention relates to devices for severely physically impaired individuals—especially children—and, more particularly, to a coordinational support for assisting people with muscle control difficulties due to cerebral palsy, for example, in performing essential, routine and everyday hand and arm functions such as writing, drawing, eating, and paper cutting or other manipulative tasks.

BACKGROUND OF THE INVENTION

Many severely physically handicapped persons—especially youngsters—have extreme difficulty performing everyday functions that normal children take for granted. Many of these people may suffer from gross motor control problems that affect their ability to write, draw, eat and move their limbs.

Therapeutic aids have been developed to assist these individuals in strengthening their muscles or training them to cope with handicaps. Some of these aids can be used to help in carrying out various chores. Most of these devices, however, are specifically designed to provide assistance with only one particular problem, or with only one specific task, such as writing. A device for providing therapy, especially by means of improving individuals' writing skills, is illustrated in U.S. Pat. No. 4,585,363 issued to McGuire on Apr. 29, 1986, entitled THERAPEUTIC AID. This device comprises a pivotable linkage that can be adjusted to provide selective resistance to a person trying to move a pencil or pen about a paper or a work surface.

The above-mentioned invention is not unlike the therapeutic device of the present invention, in that it also has pivotable linkages that can assist a patient or individual with writing. The present invention, however, features far greater versatility and universality, in that it provides means for allowing the user to do useful work by actually performing a multiplicity of tasks.

The present invention was designed primarily for children but could also be adapted for adults. The inventor has discovered that physically impaired children often must adapt themselves to an enabling device rather than having the device adapt to them. This is why the invention was made to be so versatile. If the person using the device has good fine motor control, required to hold a pencil, crayon or spoon, for example, but cannot control the spastic movements in his or her arms, a wrist restraint gives the extra support for completing the tasks while the invention dampens and eliminates unwanted movements. If the person using the device does not have refined fine motor skills, but can hold onto the object, then the use of a writing stylus or cutting tool makes it possible to do the otherwise impossible tasks of writing, coloring, drawing, cutting, etc. Even if grasping the stylus or cutting tool is difficult, Velcro® straps can be used to help hold the hand in place. Another versatile aspect is that a nut on the middle joint of the device can be tightened so that the user works in the horizontal plane only. This helps to dampen or eliminate unwanted upward movements of the user's arm. Likewise, if found necessary, the user can operate in the vertical plane exclusively.

The device in the aforementioned U.S. Pat. No. 4,585,363 has a middle joint that is positioned above the table. In this position, the middle joint has the disadvantage of restricting, rather than facilitating the movement needed to feed oneself. The middle joint taught in this patent does not allow for arcuate movement towards the mouth, which is necessary for feeding. This middle joint can also accidentally come dangerously close to an eye or other facial feature.

Another impediment against feeding in the above described, patented device is its barrel handle. This handle is designed exclusively for writing control. The person using this device cannot feed himself or herself because the hand is not free to grasp food.

Another disadvantage of the patented device is that it uses ball joints. The upper control knob positioned on top of the middle joint prevents movement in all directions once the ball joint is tightened. Therefore, it cannot move in arcuate paths for feeding purposes, once it is engaged in a writing function.

By contrast, the device of the present invention uses disks at the joints, which provide for more selectivity of movement. The middle joint of the present device is positioned on a flat work surface, which helps a child to move a pen or pencil or cutting blade more easily about the work surface. Also, because the middle joint is disposed on the work surface, more stability is provided when the wrist restraint is in the vertical plane. The end of the linkage is provided with a wrist attachment for securing the wrist of the child. This allows the hand of the youngster to reach alternately for food or for a writing implement. Thus, the child can first grip a writing device, and thereafter let go of the stylus in order to grasp food adjacently placed thereto.

In addition to writing and eating, the device of the present invention can also be fashioned with a cutting or shaping tool attachment for making paper cut-outs. The fingers of the child are protected from sharp surfaces of the cutting blades by means of a circular guard plate. The cutting blade is designed to swivel like a castor, to provide the child with greater mobility in performing the cutting task.

The inventive device has the capability of selectively restricting movement in a more facile manner than the aforementioned patented device. The present invention has, as one of its main purposes, to provide a multiplicity of functions that the handicapped child can perform using the same therapeutic apparatus.

The present invention features improvements over the device that was the subject of the aforementioned parent application, which features make the apparatus more facile. The present invention is more easily assembled and disassembled than its parent. The middle joint of the device of this invention has an interchangeable arm with spring tension that helps lift the user's arm to facilitate eating, thereby providing a range of linkage control to suit the ability of the user. The cutting tool now has one or two wheels to provide stability as it is moved across the table. The tool at the end of the linkage is now illuminated by means of a penlight and an adjustable fiber optic cable. The fiber optics adjust to intensify and direct light towards the work surface. The present invention also features an improved wrist support that is movable through a complete 360° of rotation.

SUMMARY OF THE INVENTION

In accordance with the present invention, there is provided a device that assists the motor control of a user by providing a coordinational support in all three orthogonal planes. The support comprises a linkage that can be manipulated in both the horizontal plane and the vertical plane. This versatility provides the child with the capability of performing multiple tasks. The support linkage includes a substantially flat base that supports a first housing containing a first rotatable cylinder or disk therein. The first rotatable cylinder or disk is free to rotate in the first housing through approximately 350° of arc.

Attached to the first rotatable cylinder or disk is a first, telescoping extension arm. The first telescoping extension arm terminates at a rotative collar that is orthogonally, rotatably attached to a second housing containing a second rotatable cylinder or disk that is free to rotate in the second housing through approximately 350° of arc. Combined with the housing is a spring tensioned rotative collar that adjusts the force in the orthogonally rotative direction with respect to the second housing.

Attached to the second rotatable cylinder and spring tensioned rotative collar is a second telescoping extension arm having a terminus for attaching various tools and appurtenances (such as writing instruments, cutting tools, a wrist restraint, etc.) thereto. A first resistance knob is positioned on top of the first housing for resistively adjusting the force needed to rotate the first cylinder or disk. A second resistance knob is positioned on top of the second housing for independently, resistively adjusting the force needed to rotate the second cylinder or disk. An adjustment nut is attached to the rotative collar to adjust the resistive force required to orthogonally rotate the second housing with respect to the collar.

The present invention is more easily assembled and disassembled than its parent. The addition of a Belleville disc spring gives the invention more variableness in the resistance adjustment.

The cutting tool of the current invention is now provided with one or two wheels to produce a greater stability as it is moved across the table.

The tools at the end of the linkage are now illuminated by means of a penlight and an adjustable fiber optic cable, the fiber optics adjusting to intensify and direct light towards the work surface.

The present invention also features an improved wrist support that is movable through a complete 360° of rotation.

It is an object of this invention to provide an improved device for aiding physically impaired children to perform tasks such as writing, drawing, eating and cutting.

It is another object of the invention to provide an improved therapeutic device for assisting a youngster in coordinating arm and hand movements to perform various tasks.

It is a further object of this invention to provide an improved coordinational device that has movement in both horizontal and vertical planes.

It is yet another object of the invention to provide an improved device that allows a youngster to move with ease and facility in three dimensional space.

It is also another object of the invention to provide an improved device that helps lift the youngster's arm when performing such tasks as eating or using a slant board.

BRIEF DESCRIPTION OF THE DRAWINGS

A complete understanding of the present invention may be obtained by reference to the accompanying drawings, when considered in conjunction with the subsequent detailed description, in which:

FIG. 2 depicts an exploded perspective view of the improved therapeutic device of this invention featuring the ease of assembly and disassembly of the individual parts of the apparatus;

FIG. 2a shows an interchangeable spring arm for use with the present invention;

FIG. 9 shows an exploded view of the interchangeable spring arm shown in FIG. 2a.

For purposes of clarity and brevity, like components and elements will bear the same designation and numbering throughout the Figures.

DESCRIPTION OF THE PREFERRED EMBODIMENT

Generally speaking, the invention features a device for assisting the motor control of a user. The device features a coordinational support, comprising a linkage that can be manipulated in both the horizontal and vertical planes. This versatility provides the child with the capability of performing multiple tasks.

Figure 1:
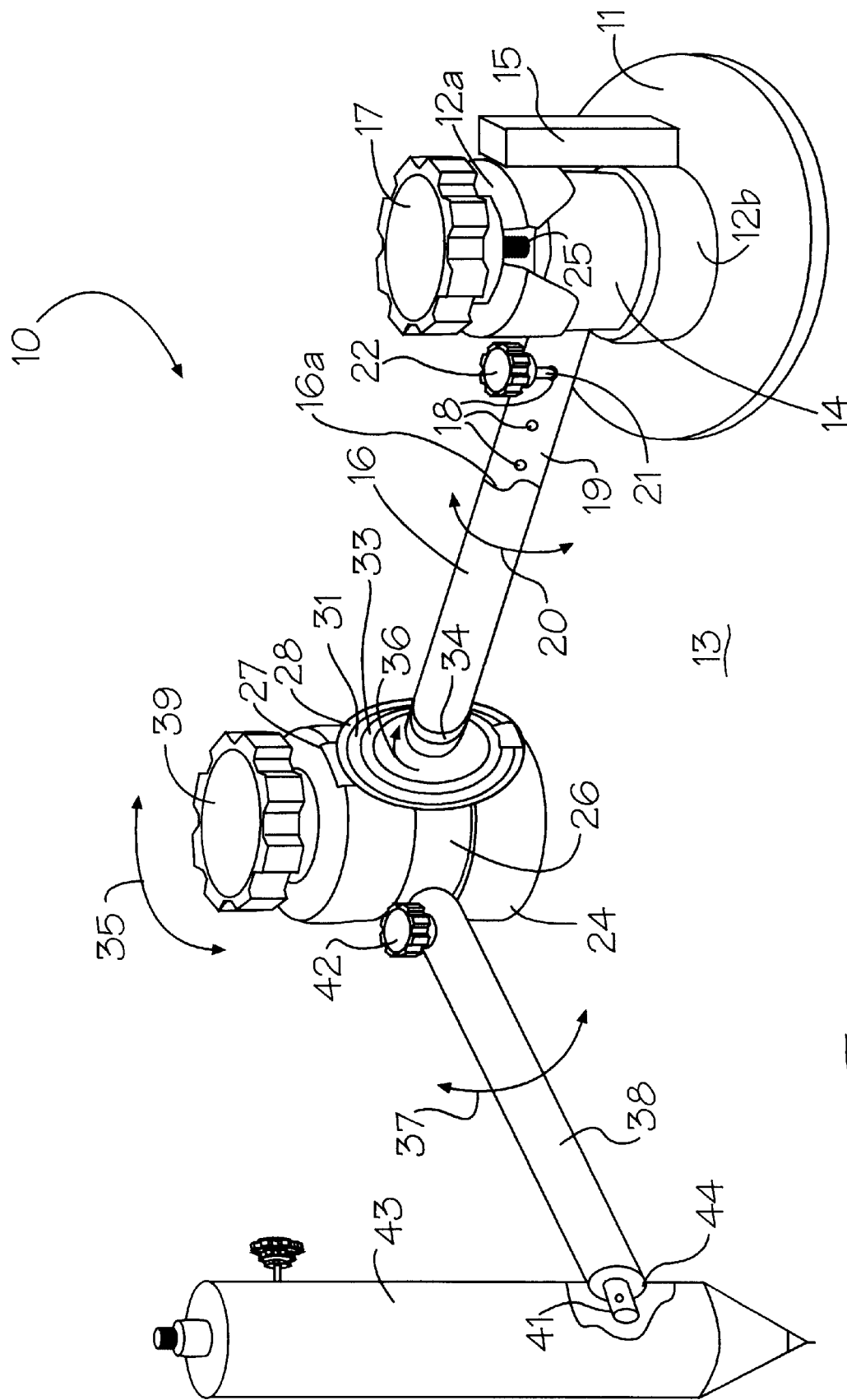
FIG. 1 illustrates a partially cut-away, perspective view of the parent device of this invention featuring a writing tool disposed at the end of its linkage.

Now referring to FIG. 1, a partially cut-away view of the parent device 10 is shown. The device 10 comprises a generally flat base 11 that rests upon a work surface 13. The flat base 11 can be anchored or secured to a portion of the work surface 13 by suitable means (e.g., a clamp) to provide more stability to the device. The flat base 11 supports a housing having an upper portion 12a and a lower or bottom portion 12b, shown partially cutaway to reveal the rotatable disk 14 disposed therein. The disk 14 rotates within the housing 12a and 12b through an arc of approximately 350°. This rotational movement is limited by the vertical stop 15 that limits the relative arcuate movement (arrows 20) of the telescoping extension arm 16 attached to disk 14.

A resistance adjustment knob 17 is shown disposed on top of the upper housing 12a. The resistance adjustment knob 17 has a screw 25 that is threaded through the disk 14 and into the bottom housing 12b. Rotatively tightening the knob 17 will draw the top housing 12a down against the disk 14, and the disk 14 against the bottom housing 12b, thus causing more frictional resistance to be created between these two elements.

The extension arm 16 is a telescoping arm for accommodating children of different sizes. The extension arm 16 is shown partially cutaway to reveal the inner rod 19 that is affixed to disk 14. The outer casement of extension arm 16, shown on edge at reference numeral 16a, slides over the inner rod 19. The inner rod 19 has a number of spaced-apart, indexed holes 18 that receive the threaded shaft 21 of knob 22. When the proper length is selected, the extension arm 16 is locked into place by the appropriate hole 18, via the threaded shaft 21 of knob 22.

A second housing 24 is disposed at the end of the extension arm 16, as illustrated. A disk 26 is disposed within the housing 24, and operates in the same fashion as does the aforementioned disk 14. The rotation of disk 26 within housing 24 is limited to an arc of approximately 280°, by reason of the stop 27 disposed on the side of the housing 24, which limits the rotation (arrows 37) of the extension arm 38, attached to disk 26. The adjustment knob 39 resting upon the top portion of housing 24 is designed identically as is knob 17, and acts in similar fashion to adjust the resistance of the disk 26 with respect to housing 24.

A rotatable collar 28 is attached to the stop 27. A hole 30 disposed in the collar 28 accepts a knobbed end 29 of extension arm 16. The knobbed end 29 is rotatively trapped within a hole 30 of collar 28, wherein the entire housing 24 can orthogonally rotate about extension arm 16, as shown by arrows 35.

A nylon spacer 31 fits on top of the collar 28, and protects the facial surface 32 of collar 28, when the adjustment nut 33 is turned (arrow 36) upon end threads 34 of extension arm 16. Rotatively tightening the adjustment nut 33 upon the collar 28 (arrow 36) via threaded portion 34 of extension arm 16 increases the frictional engagement between the housing 24 and the extension arm 16. In this manner, the orthogonal rotation of the housing 24 about the extension arm 16 can be resistively adjusted by the adjustment nut 33. The adjustment nut 33 has a knurled surface 33a for providing better gripping when adjusting the nut 33.

The extension arm 38 is similar to extension arm 16, and telescopes in like manner. The knob 42 is screwed into one of the spaced-apart indexing holes of the inner rod, not shown. The end of the extension arm 38 comprises a smooth abutment 41 that fits within a bore, not shown, of writing implement 43. The smooth abutment 41 can be affixed to the writing implement 43 by a pin, not shown, that is pushed through the outside skin of implement 43, and traverses hole 44 in the abutment 41.

The smooth abutment 41 of extension arm 38 can also fit within a smooth bore of a wrist restraint, described hereinbelow. For purposes of this disclosure, all manner of implements, restraints, and supports are called "tools." The tools are attachable to the distal end of shaft 38.

Now referring to FIG. 2, the improved therapeutic device 100 of this invention is illustrated. The improved device 100 now features an easily assembled and disassembled apparatus that comprises the base 11, the telescoping extension arms 16 and 38, frictional disks 114, 115, Belleville disc springs 116, and adjustment knobs 117, respectively. Referring now to FIG. 2a, the interchangeable spring arm 101 contains an internal, torsion spring 105 (FIG. 9) against which the knuckle 110 can be rotated (arrow 112) with respect to knuckle 111. The internal spring 105 provides positive tension biasing, which the previous friction plate 31 of the parent device lacked. The spring 105 can be obtained from Lee Spring of Brooklyn, N.Y. or Associated Spring Co. The torsion spring 105 has a 180° deflection. The spring constant can represent different force to customize the system to the individual, such as: 5, 7, and 9.75 pounds, etc, so that, when used with the wrist support 130 (FIG. 8) or the forearm support 140 (FIG. 7), the spring tension helps lift the individual's arm.

Figure 3:
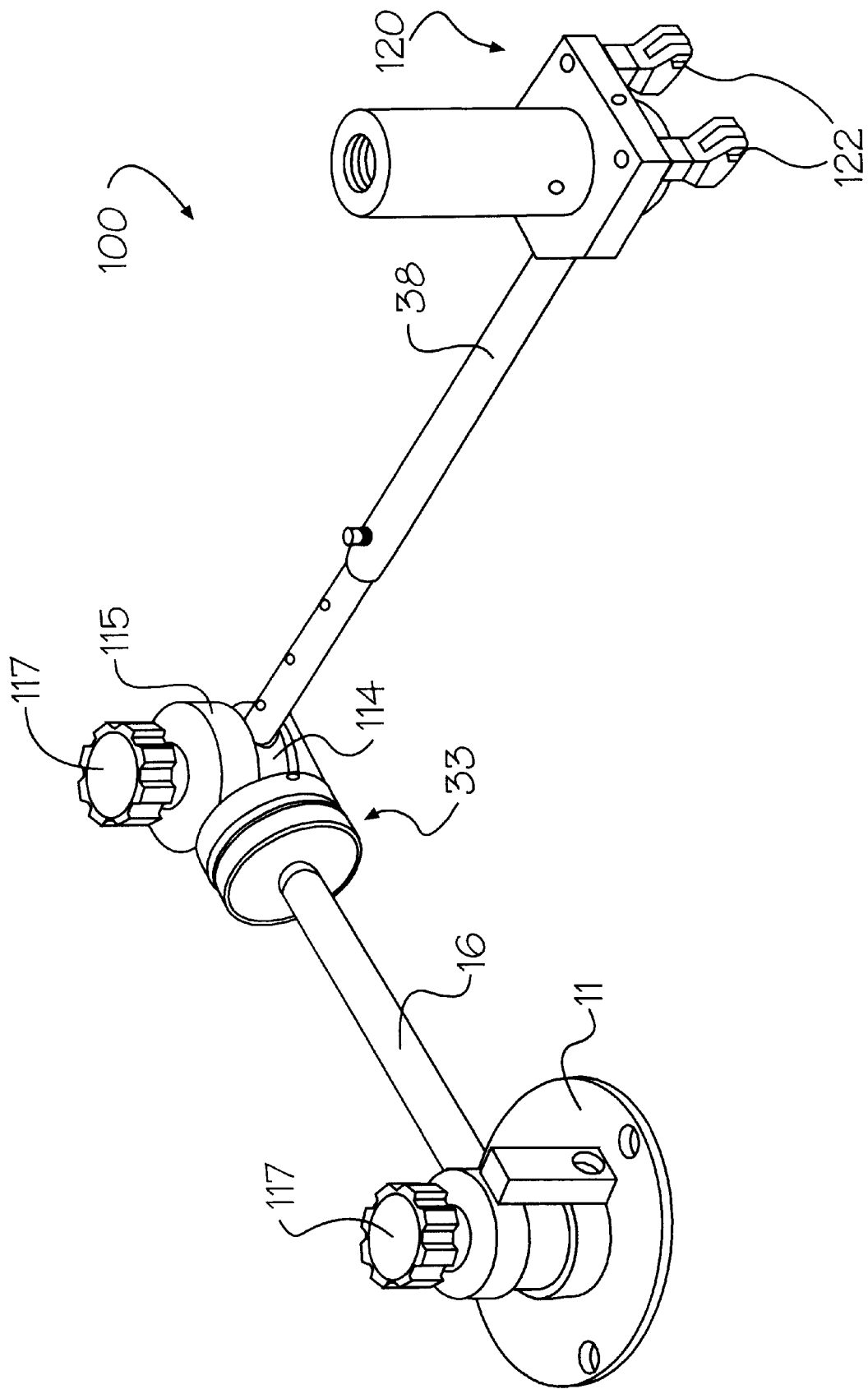
FIG. 3 shows a perspective view of the improved therapeutic device of this invention having a cutting tool that has rollers attached thereto for stability.

Referring to FIG. 3, the improved device 100 shown in FIG. 2 is illustrated with a cutting tool attachment 120 that comprises two rollers 122. The rollers 122 provide stability of movement, which is most useful when using a cutting tool.

Figure 4:
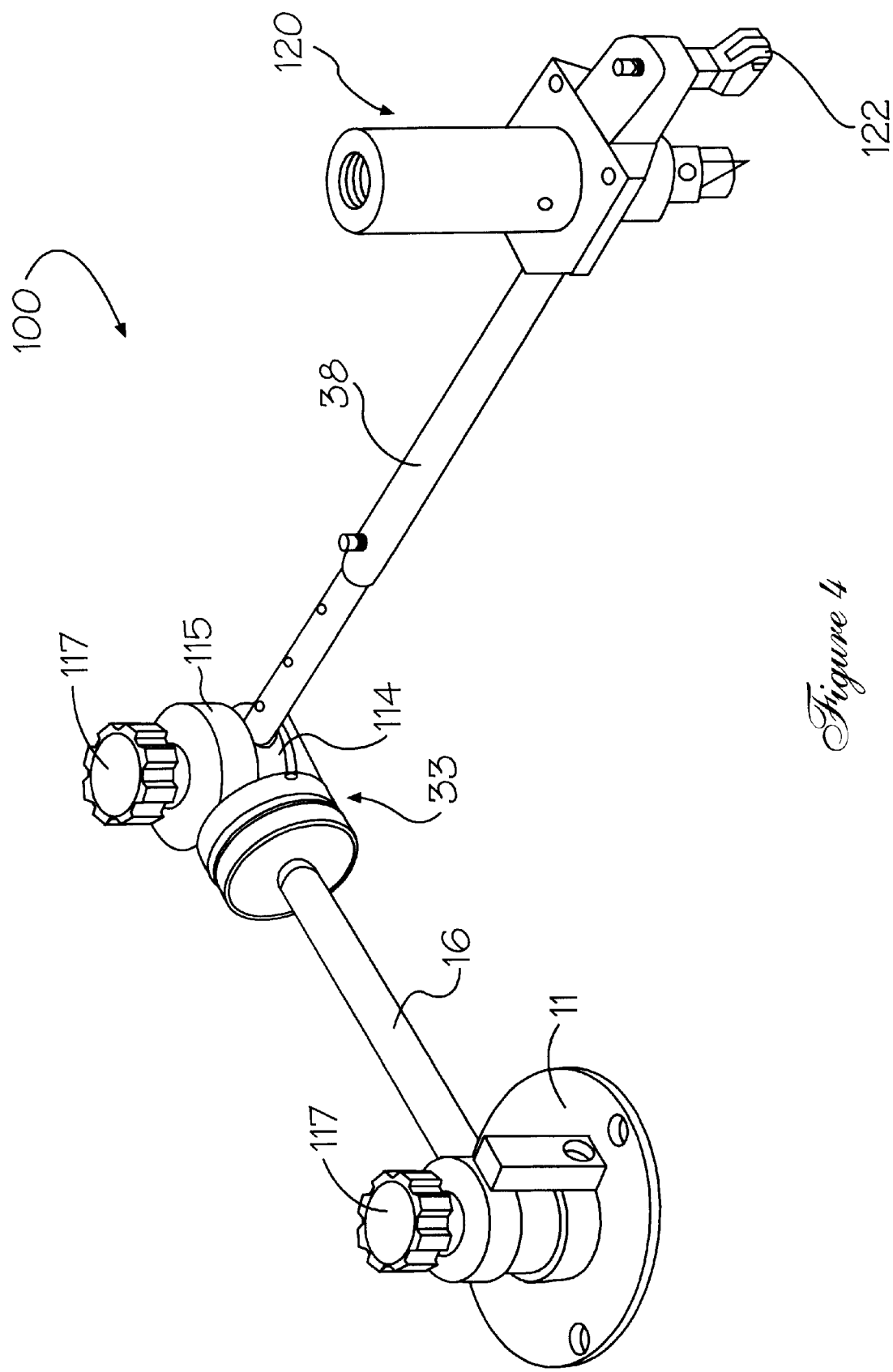
FIG. 4 depicts a perspective view of the improved therapeutic device with a cutting tool, as illustrated in FIG. 3, but now featuring a single roller.

Referring to FIG. 4, an alternative embodiment of the improved device 100 shown in FIG. 2 is illustrated with a cutting tool attachment 120 that comprises one roller 122. A single roller 122 is easier to guide, and can be utilized with individuals who have greater control. Also, a single roller 122 provides better visibility of the work surface.

Figure 5:
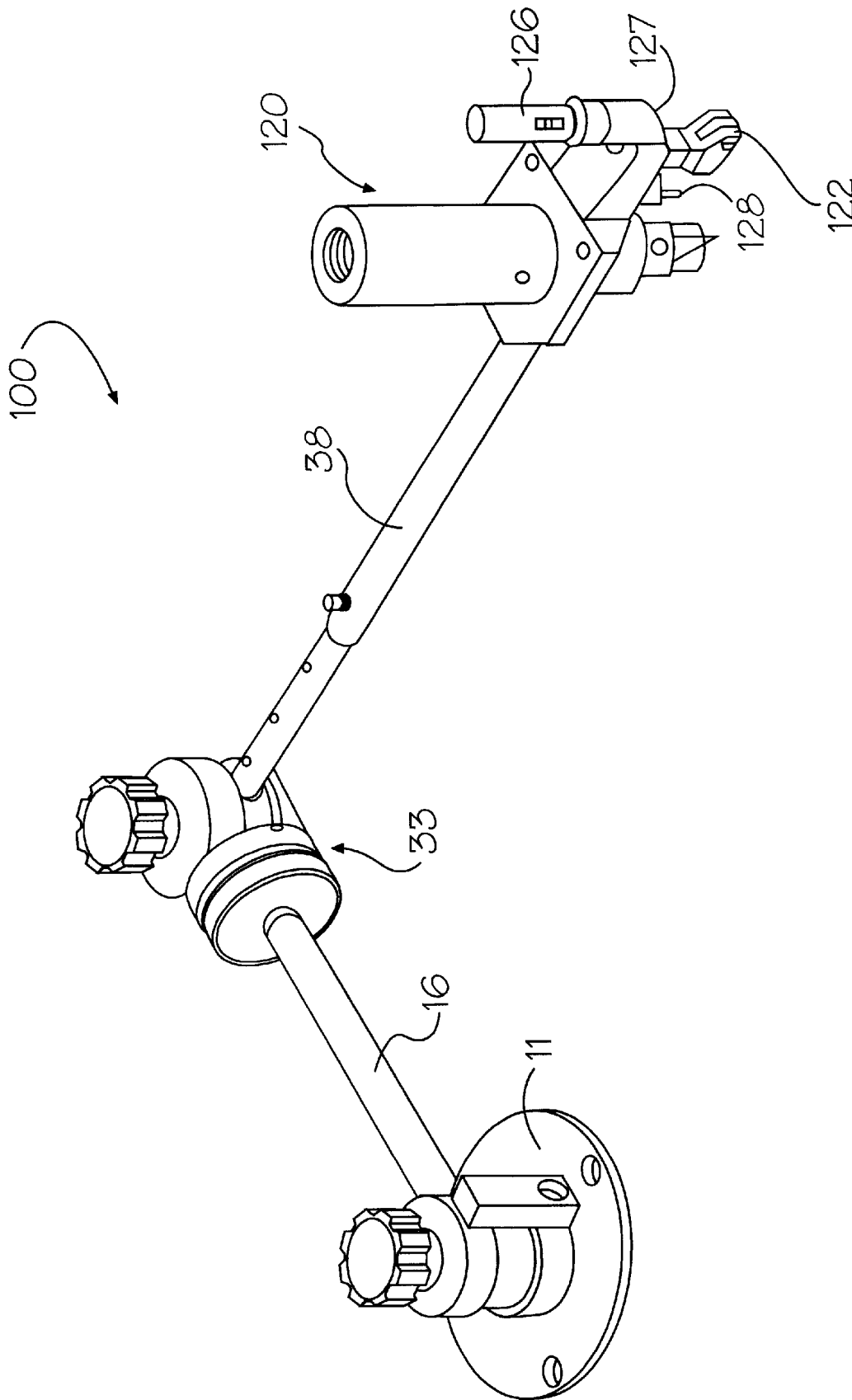
FIG. 5 illustrates a perspective view of the improved therapeutic device with a cutting tool, as illustrated in FIG. 3, but now featuring a light attachment.

Referring to FIG. 5, the improved device 100 shown in FIG. 2 is illustrated with a cutting tool attachment 120 that comprises a penlight 126 with a focusing cap 127. A fiber optic wire 128 can direct the light provided by the penlight 126 to different areas of the work surface.

Figure 6:
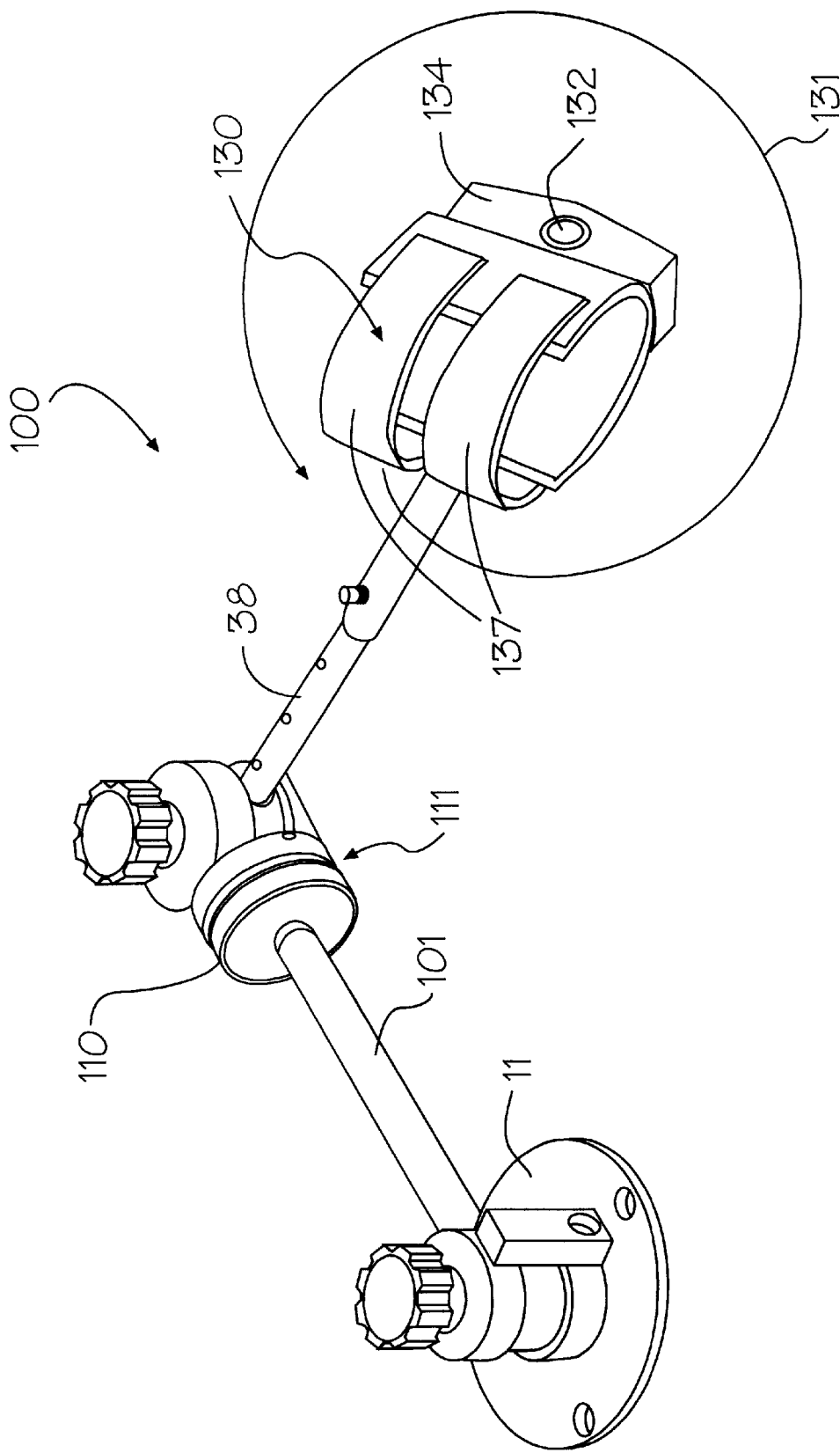
FIG. 6 shows a perspective view of the improved therapeutic device of FIG. 2 featuring an improved wrist support.

Referring to FIG. 6, the improved device 100 shown in FIG. 2a is illustrated with a wrist support 130. The wrist support 130 is movable through an arc of 360°, as illustrated by arrow 131. The wrist support 130 is mounted upon base 134 that is attached to arm 38 by mounting shaft 132, as shown. The base 134 rotates about shaft 132, giving the wrist support 130 its arcuate movement. The support 130 captures the wrist of the child. The strapping 137 contains heavy duty Velcro® attachment pads and allows the child to grasp food or other materials while being guided and supported by device 100.

Figure 7:
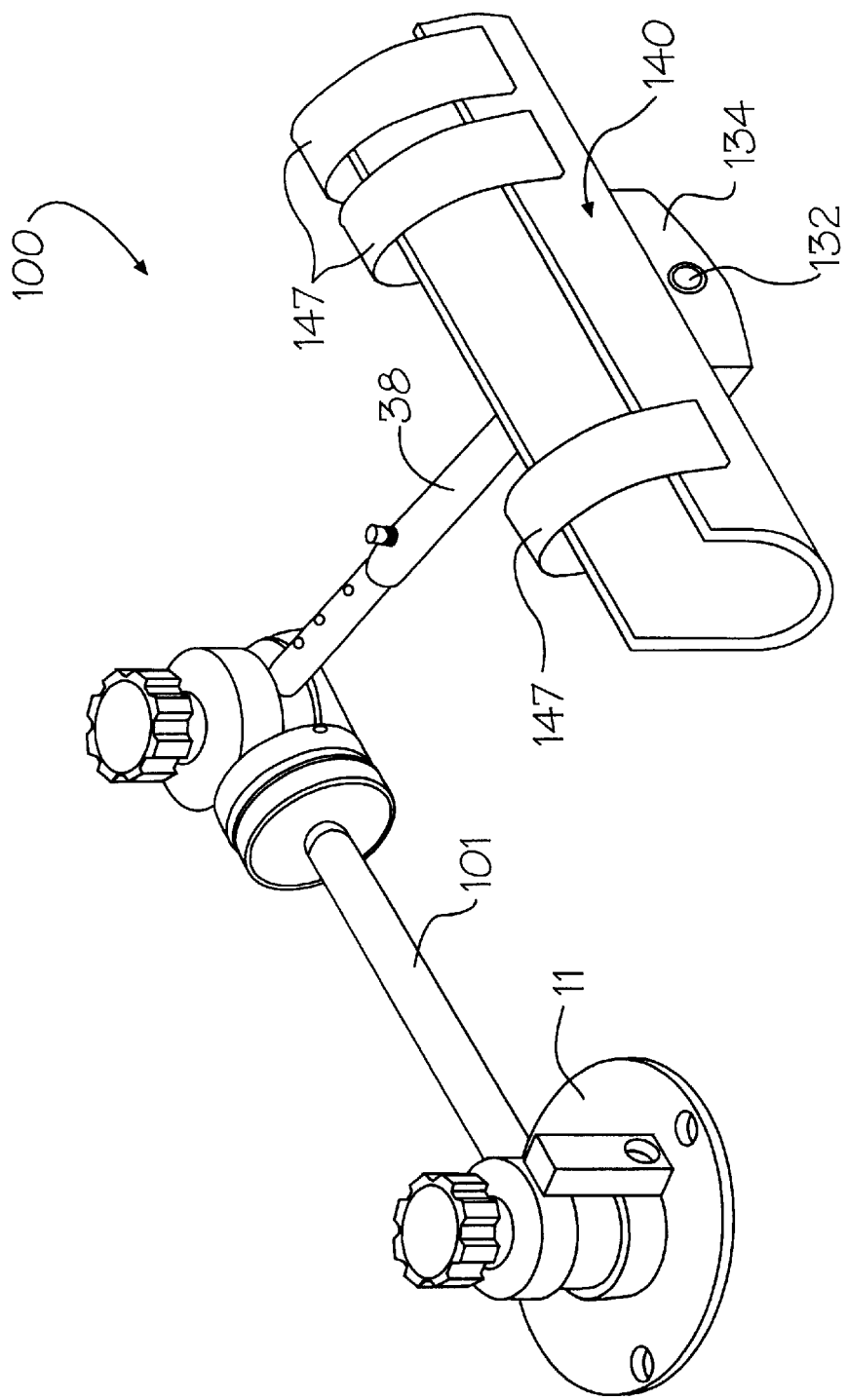
FIG. 7 depicts a perspective view of the improved therapeutic device of FIG. 2 featuring an improved forearm support.

Referring to FIG. 7, the improved device 100 shown in FIG. 2a is illustrated with a forearm support 140. The forearm support 140 is similar to the wrist support 130, and is also movable through an arc of 360° by means of base 134 that is attached to arm 38 by mounting shaft 132, as shown. The strapping 147 contains heavy duty Velcro® attachment pads and allows the child to grasp food or other materials while being guided and supported by device 100.

Figure 8:
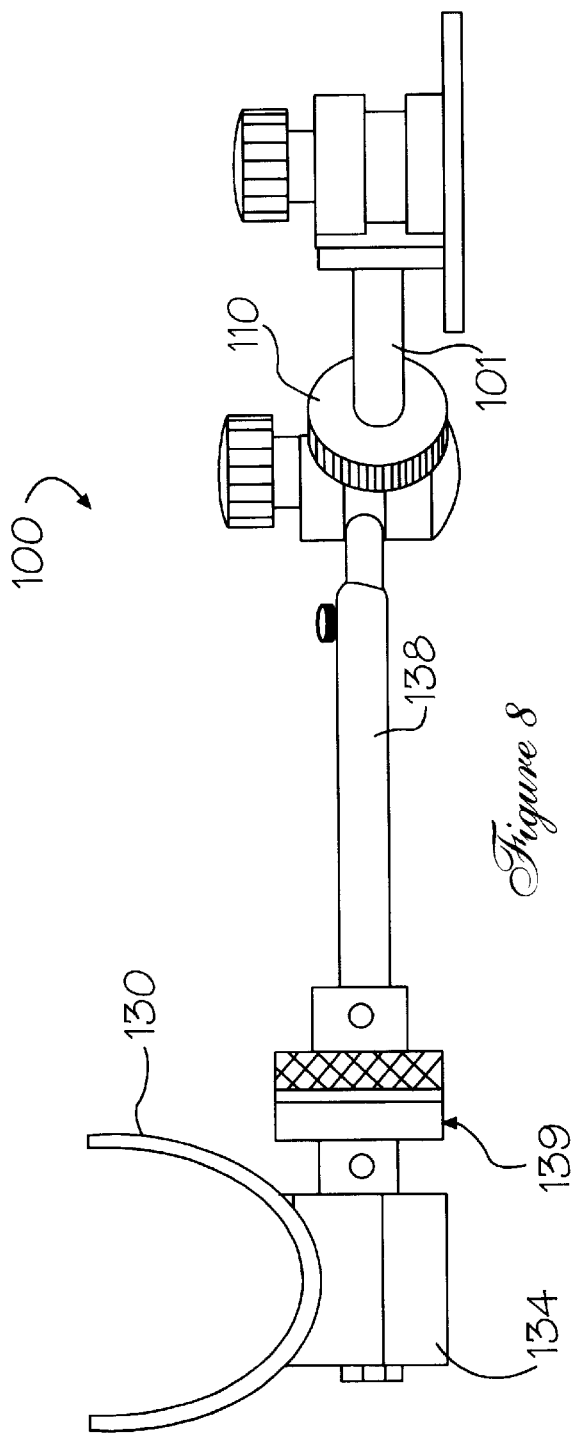
FIG. 8 illustrates a front view of the improved therapeutic device with wrist support, shown in FIG. 6.

Referring to FIG. 8, the wrist support apparatus 130 of FIG. 6 is shown in a frontal view. The wrist support is attachable to the shaft 38 through an adjustment nut 139, similar to the adjustment nut 33. The adjustment nut 139 is shown in exploded view in FIG. 8a. A dowel pin 152 and set screw 151 anchor and tighten the link 153 to the wrist support base 134, by means of a groove 153a in link 153. The adjustment nut 139 is shown with a friction plate 154. The knurled knob 155 that screws upon threads 156 of the link 153 adjusts the frictional force of the friction plate 154. It should be observed that the above adjustment can also apply to the forearm support 140.

Figure 8A:
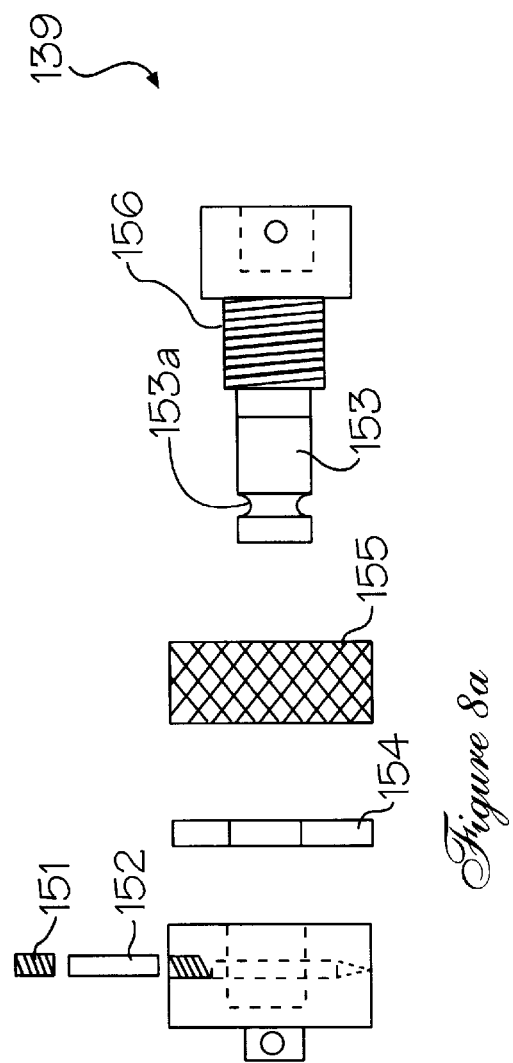
FIG. 8a shows a front, exploded view of the adjustment screw apparatus for adjusting the wrist support apparatus, depicted in FIG. 8.
Figure 8B:
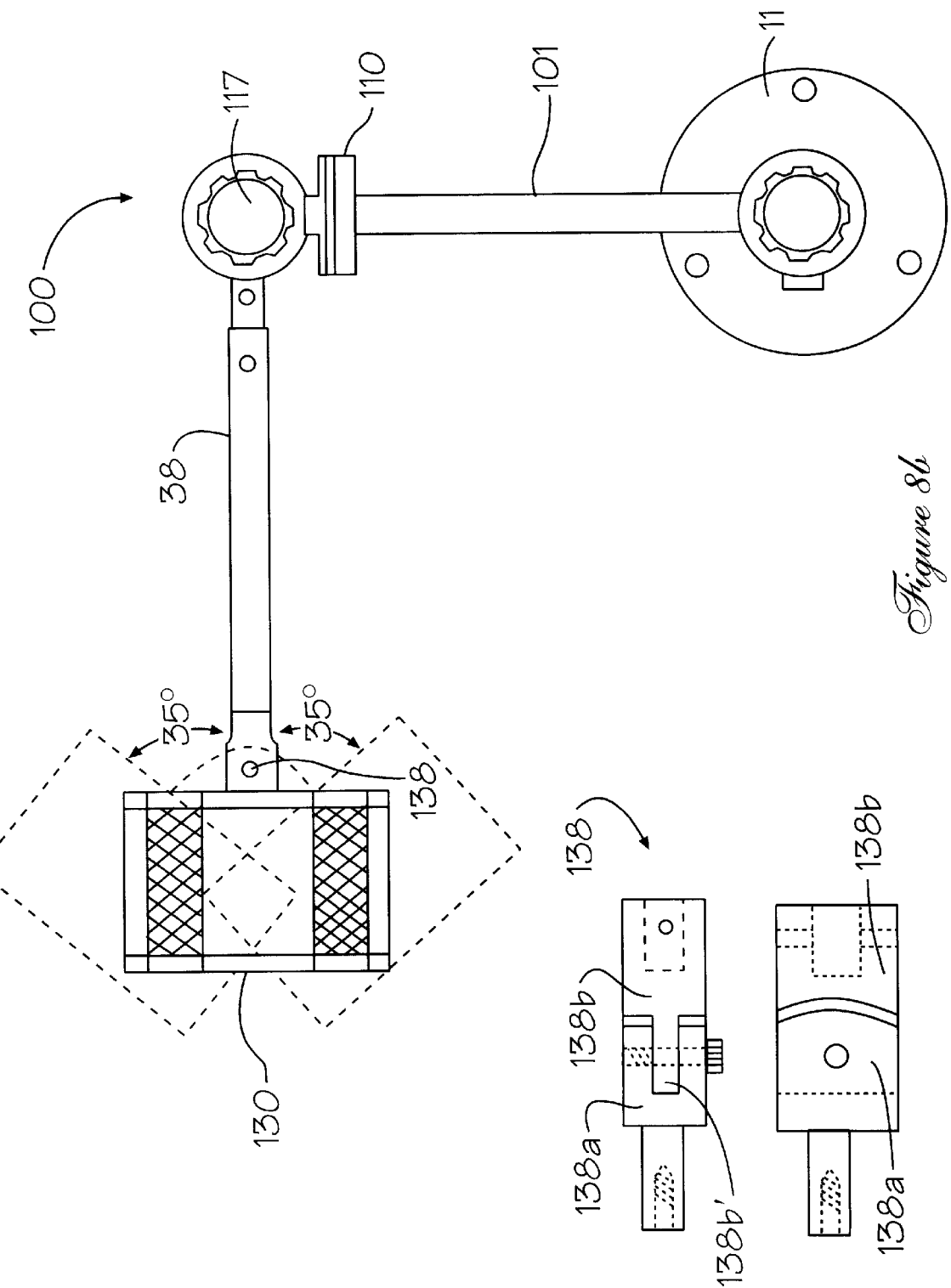
FIG. 8b is a top view of an alternate embodiment of the inventive apparatus, showing a pivot mechanism at the wrist portion thereof.

In an alternate embodiment, shown in FIG. 8b, pivotally connected to the distal side of extension arm 38 is wrist support 130 and 134 (FIG. 8). Wrist support 130 and 134 is mounted to arm 38 by means of a pivot mechanism 138, consisting of a bifurcated yoke 138a, pivotal mating component 138b (which has a suitable protuberance 138b'), and cap screw 138c for adjusting tension. In operation, the user can flex his or her wrist by pivoting wrist support 130 and 134 up to approximately ±35° relative to the major axis of extension arm 38.

Figure 9:
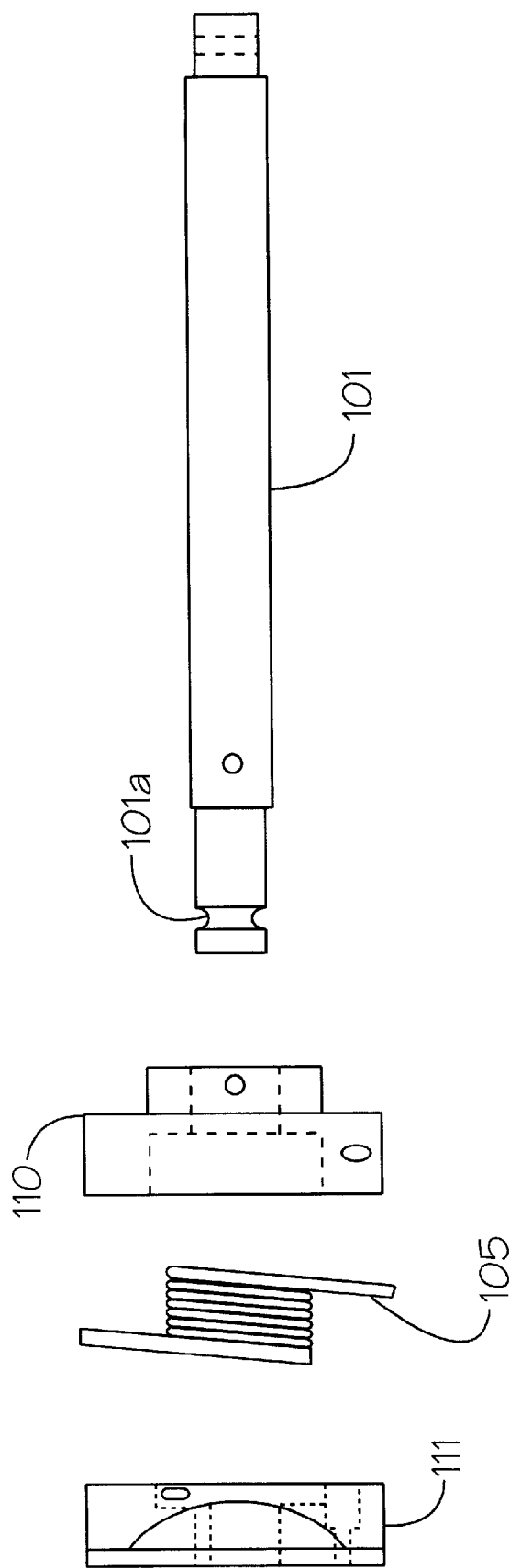

FIG. 9 shows an exploded view of the interchangeable spring arm 101, shown in FIG. 2a. Torsion spring 105 is contained in the housing formed by knuckles 110 and 111, as shown. Also shown in FIG. 9 is the interchangeable spring arm 101, having a groove 101a for receiving dowel pin 152 (FIG. 8a).

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. An easily assembled and disassembled support for an individual, said support having linkage elements which are secured to each other by threaded fastening means, comprising:

a base;

a linkage connected to said base that can be manipulated in a horizontal plane, including a first housing containing a first rotatable disk therein, said first rotatable disk being free to rotate in the first housing about said horizontal plane;

a first extension arm attached to said first rotatable disk for rotating therewith, said first extension arm extending to a second housing;

a second housing that is orthogonally rotatable with respect to said first extension arm providing movement of said second housing in said vertical plane with respect to said first housing, said second housing containing a second rotatable disk therein, said second rotatable disk being free to rotate in said second housing about said horizontal plane;

adjustment means adjacent to said second housing for adjusting the orthogonal rotative force of movement about said second housing, said adjustment means being internally, torsionally spring biased; and a second extension arm attached to said second rotatable disk and comprising means for securing at least two tools thereto.

2. The support in accordance with claim 1, wherein said first and second linkages are free to rotate in said horizontal plane through a composite arc of 360°.

3. The support in accordance with claim 1, further comprising means disposed upon each housing for independently adjusting rotative resistance of said respective first and second rotatable disks.

4. The support in accordance with claim 1, wherein at least one of said first and second extension arms comprises telescoping means.

5. The support in accordance with claim 1, further comprising a forearm support attachment that it arcuately attached to said second extension arm.

6. The support in accordance with claim 1, further comprising a wrist support attachment that is arcuately attached to said second extension arm.

7. The support in accordance with claim 1, further comprising a wrist support attachment that is pivotally attached to said second extension arm.

8. An easily assembled and disassembled support for an individual, the linkage elements of which are secured to each other upon threaded surfaces, and which allows said individual to perform a function requiring movement in all three orthogonal dimensions, said support comprising:

a linkage that can be manipulated in a horizontal plane and a vertical plane, including a substantially flat base that supports a first housing containing a first rotatable disk therein, said first rotatable disk being free to rotate in the first housing about said horizontal plane;

a first extension arm attached to said first rotatable disk and rotating therewith, said first extension arm extending to a second housing;

a second housing that is orthogonally rotatable with respect to said first extension arm providing movement of said second housing in said vertical plane with respect to said first housing, said second housing containing a second rotatable disk therein, said second rotatable disk being free to rotate in said second housing about said horizontal plane;

adjustment means adjacent to said second housing for adjusting the orthogonal rotative force of movement about said second housing; and a second extension arm attached to said second rotatable disk and comprising means for securing at least two tools thereto, one of which comprises a cutting tool attachment that has at least one roller support.

9. The support in accordance with claim 8, further comprising a forearm support attachment that is arcuately attached to said second extension arm.

10. The support in accordance with claim 8, further comprising a wrist support attachment that is arcuately attached to said second extension arm.

11. The support in accordance with claim 8, further comprising a wrist support attachment that is pivotally attached to said second extension arm.

12. The support in accordance with claim 8, further comprising means disposed upon each housing for independently adjusting rotative resistance of said respective first and second rotatable disks.

13. The support in accordance with claim 8, wherein at least one of said first and second extension arms comprises telescoping means.

14. An easily assembled and disassembled support for allowing a user to perform a function requiring movement in three-dimensional space, said support comprising:

a base; and a linkage having elements supported by said base that are threaded together in an easily assembled manner, and that can be manipulated in three-dimensional space, said elements including a first rotatable extension arm, said first extension arm extending to a second extension arm, said second extension arm having means for independently, orthogonally rotating said second extension arm about said first extension arm and including a spring biased adjustment for helping to move said second extension arm in a vertical plane, said second extension arm comprising means for securing a tool thereto, said tool being threadably attachable at a distal end of said second extension arm.

15. The support in accordance with claim 14, wherein said first and second linkages are free to rotate in a horizontal plane through a composite arc of 360°.

16. The support in accordance with claim 14, wherein at least one of said first and second extension arms comprises telescoping means.

17. The support in accordance with claim 14, further comprising a forearm support attachment that is arcuately attached to said second extension arm.

18. The support in accordance with claim 14, further comprising a wrist support attachment that is movably attached to said second extension arm.

* * * * *